US005498872A

United States Patent [19]
Stedman et al.

[11] Patent Number: 5,498,872
[45] Date of Patent: *Mar. 12, 1996

[54] APPARATUS FOR REMOTE ANALYSIS OF VEHICLE EMISSIONS

[75] Inventors: Donald H. Stedman, Denver; Gary Bishop, Louisville; Scott McLaren, Denver, all of Colo.

[73] Assignee: Colorado Seminary, Denver, Colo.

[*] Notice: The portion of the term of this patent shall not extend beyond the expiration date of Pat. No. 5,210,702.

[21] Appl. No.: 426,910

[22] Filed: Apr. 21, 1995

Related U.S. Application Data

[63] Continuation of Ser. No. 275,950, Jul. 15, 1994, abandoned, which is a continuation of Ser. No. 253,749, Jun. 3, 1994, Pat. No. 5,401,967, which is a continuation-in-part of Ser. No. 895,342, Jun. 8, 1992, Pat. No. 5,319,199, which is a continuation-in-part of Ser. No. 633,952, Dec. 26, 1990, Pat. No. 5,210,702.

[51] Int. Cl.$^6$ .......................... G01N 21/00; G01N 21/17
[52] U.S. Cl. .................. 250/338.5; 250/339.13; 356/438
[58] Field of Search .................. 250/338.5, 339.13, 250/339.12; 356/438

[56] References Cited

U.S. PATENT DOCUMENTS

| | | |
|---|---|---|
| 2,930,893 | 3/1960 | Carpenter et al. . |
| 3,171,027 | 2/1965 | Wallack . |
| 3,287,556 | 11/1966 | Good . |
| 3,364,351 | 1/1968 | Palmer et al. . |
| 3,696,247 | 10/1972 | McIntosh et al. . |
| 3,958,122 | 5/1976 | Jowett et al. . |
| 3,973,848 | 8/1976 | Jowett et al. . |
| 4,126,396 | 11/1978 | Hartmann et al. . |
| 4,160,373 | 7/1979 | Fastaia et al. . |
| 4,348,732 | 9/1982 | Kreft . |
| 4,390,785 | 6/1983 | Faulhaber et al. . |
| 4,490,845 | 12/1984 | Steinbruegge et al. . |

(List continued on next page.)

FOREIGN PATENT DOCUMENTS 54-5778 1/1979 Japan .

OTHER PUBLICATIONS

Bishop, Gary A., et al., "IR Long–Path Photometry: A Remote Sensing Tool for Automobile Emissions," Am. Chem. Soc., 1989, pp. 671A–676A.

Chaney, Lucian W., "The Remote Measurement of Traffic Generated Carbon Monoxide," J. Air Pollut. Control Assoc., Mar. 1983, pp. 220–222.

Stedman, Donald H., "Automobile Carbon Monoxide Emission," Environ. Sci. Technol., 1989, pp. 147–149.

Peterson et al., "Find and Fix the Polluters", Chemtech, Jan. 1992, pp. 47–53.

Primary Examiner—Carolyn E. Fields
Assistant Examiner—Edward J. Glick
Attorney, Agent, or Firm—Dorr, Carson, Sloan & Birney

[57] ABSTRACT

A gas analysis device for the remote detecting, measuring and recording of NO, CO, $CO_2$, HC, and $H_2O$ levels from the exhaust (30) of moving motor vehicles (28) utilizes a source (11) of collimated infrared and ultraviolet radiation (15) and includes a detector unit (16) positioned on the opposite side of the roadway for receiving and measuring the infrared and ultraviolet radiation from the source (11) tranmitted through the vehicle exhaust. The detector unit splits the combined infrared and ultraviolet radiation into separate infrared and ultraviolet beams (42) and (40). The ultraviolet beam is diffracted onto a photodiode array in a spectrometer that generates a signal indicative of NO in the vehicle exhaust. A rotating reflector (27) time-multiplexes the infrared beam to a plurality of infrared sensors that generate electrical signals indicative of, for example, CO, $CO_2$, HC, and $H_2O$ in the vehicle exhaust. A computer (17) then computes the relative concentrations of CO, $CO_2$, HC, NO, and $H_2O$ in the path of the infrared and ultraviolet radiation from the source, thereby measuring vehicle emissions.

18 Claims, 9 Drawing Sheets

U.S. PATENT DOCUMENTS

| | | |
|---|---|---|
| 4,632,563 | 12/1986 | Lord, III . |
| 4,678,914 | 7/1987 | Melrose et al. . |
| 4,746,218 | 5/1988 | Lord, III . |
| 4,755,678 | 7/1988 | Izatt et al. . |
| 4,795,253 | 1/1989 | Sandridge et al. . |
| 4,818,705 | 4/1989 | Schneider et al. . |
| 4,924,095 | 5/1990 | Swanson, Jr. . |
| 4,963,023 | 10/1990 | Goldovsky et al. . |
| 4,999,498 | 3/1991 | Hunt et al. . |
| 5,002,391 | 3/1991 | Wolfrum et al. . |
| 5,041,723 | 8/1991 | Ishida et al. . |
| 5,061,854 | 10/1991 | Kroutil et al. . |
| 5,076,699 | 12/1991 | Ryan et al. . |
| 5,210,702 | 5/1993 | Bishop et al. . |
| 5,319,199 | 6/1994 | Stedman et al. . |
| 5,401,967 | 3/1995 | Stedman et al. ............... 250/338.5 |

APPARATUS FOR REMOTE ANALYSIS OF VEHICLE EMISSIONS

The present application is a continuation in part of Applicant's U.S. patent application Ser. No. 08/275,950, filed Jul. 15, 1994, now abandoned, which is a continuation of U.S. patent application Ser. No. 08/253,749, filed Jun. 3, 1994, now U.S. Pat. No. 5,401,967, which is a continuation-in-part of U.S. patent application Ser. No. 07/895,342, filed Jun. 8, 1992, now U.S. Pat. No. 5,319,199, which is a continuation-in-part of U.S. patent application Ser. No. 07/633,952, filed on Dec. 26, 1990, now U.S. Pat. No. 5,210,702.

BACKGROUND OF THE INVENTION

Federal and state governments, along with vehicle manufacturers, test and certify new vehicle emissions, and also carry out some in-use testing of older vehicles. These tests comply with the Federal Test Procedure (FTP) as outlined in the Federal Register, which is a carefully designed and specified three-phase test under "cold transient," "cold stabilized," and "hot transient" conditions. The vehicle is generally driven in a series of accelerations, decelerations, stops, and starts on a chassis dynamometer, whose inertia and friction are specifically set for each vehicle. The emissions from each phase am collected at a constant volume into a sample bag, and the concentrations of each species of pollutant are determined from the integration of the entire bag, with a final result given in grams of pollutant per mile.

The driving course is modeled after a "typical" summertime commute to work in Los Angeles. Each of these tests takes at least twelve hours to complete and costs in excess of about $700, in 1990 dollars. The reproducibility of the results for a given vehicle is believed to be plus or minus 20%, controlled mainly by the repeatability of the vehicle emissions system and not by the test system or gas analysis protocols. Presently available computer models am based on the concept that the FTP emissions measured from a fleet of vehicles are well correlated, although not necessarily one to one, with the emissions that the same fleet would exhibit under in-use driving conditions. However, since very little is known about actual on-the-road fleet emissions, it is impossible to truly gauge the accuracy of this assumption.

In addition to any new car emission certification programs, there are also state inspection and maintenance (IM) programs designed to test every vehicle in a given area that are, therefore, much less rigorous tests. The most sophisticated centralized IM testing programs use a chassis dynamometer with one or two fixed loads and speeds and measure the steady-state emissions as a percentage of the exhaust. Many centralized, and all decentralized, programs measure only idle emissions as a percentage of the exhaust at one, or possibly two, engine speeds.

In late 1986, a fuel efficient automobile test (FEAT) system was developed and designed to remotely detect carbon monoxide and carbon dioxide levels in vehicular emissions and to make specific measurements on individual vehicles. This system is more specifically described in an article entitled "*Automobile Carbon Monoxide Emission,*" Environmental Science Technology, vol. 23, pages 147–149, 1989. Also see "*IR Long-Path Photometry: A Remote Sensing Tool for Automobile Emissions,*" Analytical Chem., vol. 61, pages 671A–676A, 1989. This particular device, while extremely accurate, had its limitations in that it was unable to identify the specific vehicles found to be emitting carbon monoxide in excess of acceptable levels so that the vehicle owner could be subsequently contacted and advised to adjust or repair or modify the vehicle to control its emissions. Moreover, while it was capable of measuring carbon monoxide and carbon dioxide, it was not capable of measuring other emission components or the temperature at which the vehicle was operating, the knowledge of which would be extremely valuable to have.

As indicated, it is known to the inventors that the basic idea of remotely measuring vehicle emissions is not a new one. Lockheed Missiles and Space Corporation first attempted construction of an across-the-road monitor, the successful operation of which was never published. L. Chaney, "*The Remote Measurement of Traffic Generated Carbon Monoxide,*" J. Air Pollution Control Association, vol. 33, pages 220–222, 1983, proved that carbon monoxide fumes (and only carbon monoxide) from passing vehicles could be observed in real-time with a gas filter correlation radiometer. However, Chaney's system did not include any of the parameters required to accurately measure emissions data from vehicle exhaust plume observations.

it would be of particular interest to measure the hydrocarbon emissions as well as nitrogen oxides and water emission levels of identifiable individual vehicles. Therefore, there is still a need for a remote sensing and measuring device to permit measurement of vehicle exhaust while the vehicles are in use. This technique or device permits the quantification of not only carbon monoxide, but also carbon dioxide, hydrocarbons, nitrogen oxides, and water vapor emissions, as well as providing the option of identifying each individual vehicle being tested by the device.

SUMMARY OF THE INVENTION

In view of the foregoing, it is one object of the present invention to provide an improved remote gas analysis device for the detection of emission levels of polluting components in vehicle exhaust.

It is another object of the present invention to provide an emissions detection device specifically designed to detect carbon monoxide, carbon dioxide, hydrocarbons, and nitric oxide simultaneously in the emissions of vehicles.

It is yet another object of the present invention to provide an emissions detection device specifically designed to simultaneously measure the operating temperature of vehicles while also measuring the amount of specific pollutants from that vehicle.

Another object of the present invention is to provide such a device that remotely detects and measures carbon monoxide, carbon dioxide, hydrocarbons, and nitric oxide emissions from in-use vehicles.

A further object of the present invention is to provide such a remote detection device that includes visual monitoring and recording capabilities so as to identify the specific vehicle both on-line and in recorded form from which specific carbon monoxide, carbon dioxide, hydrocarbon, and nitric oxide emission levels at a specific vehicle operating temperature are being measured.

The foregoing objects and advantages of the present invention are obtained by providing a gas analysis device for measuring concentrations of carbon monoxide, carbon dioxide, hydrocarbons, nitric oxide, and water in motor vehicle exhaust by utilizing a collimated beam of both infrared and ultraviolet radiation passing through the vehicle exhaust. The device includes a mechanism adapted to receive and measure the infrared and ultraviolet radiation and a device for measuring background infrared and ultraviolet radiation levels in the path of the beam in the absence of a vehicle. A device splits the combined infrared and ultraviolet radiation that is received from the atmosphere into separate infrared and ultraviolet beams. A mechanism, such as a rotating reflective surface, time-multiplexes the infrared beam into at least two and preferably three or four separate infrared beam components. A plurality of sensors are positioned for receiving each of the infrared beam components and generating electrical signals indicative of the absorption of the infrared beam in the exhaust by carbon monoxide (CO), carbon dioxide ($CO_2$), and also preferably by hydrocarbons (HC generally) and water ($H_2O$). A spectrometer is used to diffract the separate ultraviolet beam and generate an electrical signal indicative of the absorption of the ultraviolet radiation by nitric oxide (NO) in the exhaust. A computer uses the electrical signals produced by the sensors for computing and for producing output signals indicative of the amount of CO, $CO_2$, HC, NO, and $H_2O$ in the path of the collimated infrared and ultraviolet radiation in the exhaust to measure vehicle emissions.

BRIEF DESCRIPTION OF THE DRAWINGS

The accompanying drawings illustrate complete preferred embodiments of the present invention and the best modes presently devised for the practical application of the principles thereof, in which.

DETAILED DESCRIPTION OF THE INVENTION

Figure 1:
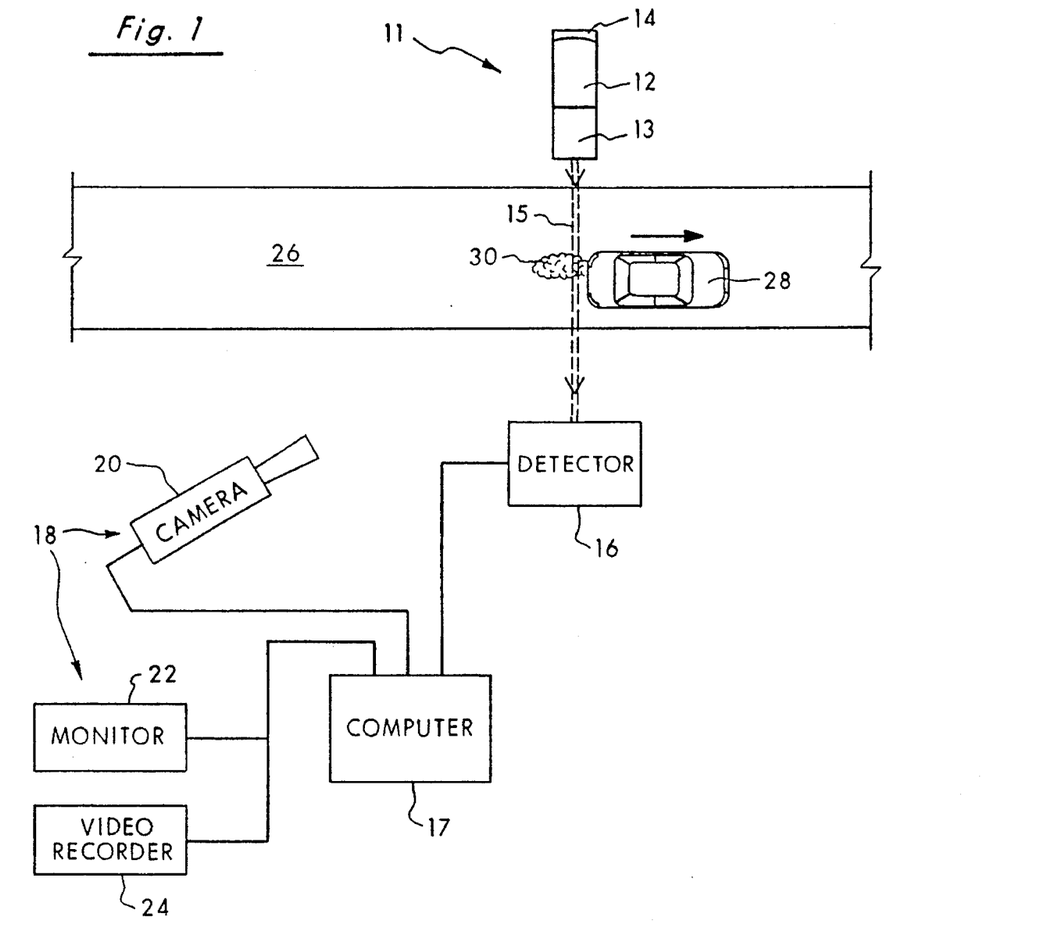
FIG. 1 is a schematic diagram of the remote measuring and monitoring system of the present invention shown in use across a roadway with one vehicle and its exhaust in a detection position.

Referring now to FIG. 1, the system includes a light source 11 made up of an ultraviolet radiation source 12, an infrared radiation source 13, a device 14 for collimating the light beams from the sources 12 and 13 into a collimated beam 15, a detector unit 16 having a computer 17, and a video monitoring system 18. The video monitoring system 18 preferably includes a video camera 20, a monitor unit 22, and a video recording storage device 24. The ultraviolet radiation source 12 and infrared radiation source 13 may be collimated, and therefore not require collimating device 14.

The present invention utilizes infrared absorption to measure the concentrations of carbon monoxide, carbon dioxide, hydrocarbons, and water added to the air by an individual passing vehicle. In addition, the system can utilize ultraviolet absorption to determine the concentration of nitrogen oxides added to the air by such a vehicle.. In one embodiment, the light source 11 is located on one side of an open space, typically a roadway 26, along which a vehicle 28 moves. The light source 11 sends a collimated beam of radiation 15 into the detector unit 16 on a continuous basis. A computer 17 continuously samples all infrared and ultraviolet beam intensities received by each of the sensors of the detector unit 16. When the beam 15 is blocked by a vehicle 28 as it passes along the roadway 26, the memory of the computer 17 retains information concerning the carbon monoxide, carbon dioxide, hydrocarbons, nitrogen oxides, and water levels in the ambient atmosphere in front of the vehicle 28 prior to the blocking of the beam 15, and then samples the carbon monoxide, carbon dioxide, hydrocarbons, nitrogen oxides, and water levels of the exhaust 30 behind the vehicle 28 for a predetermined period (e.g., about 0.1 to about 1.0 second) after resumption of reception of the beam 15 by the detector unit 16.

In one preferred embodiment, a vehicle-identifying system, such as a video camera 20, records the end view portion of the vehicle 28 (including the vehicle's license plate) simultaneously with the unblocking of the beam 15 by the vehicle 28. This is generally the rear portion of the vehicle 28, although the front or other portions of the vehicle can be recorded. When the vehicle 28 has passed the detector 16 and the exhaust 30 has been sampled, the results are compared to the carbon monoxide, carbon dioxide, hydrocarbons, nitrogen oxides, and water levels recorded prior to beam interruption, as well as to calibration plots stored in computer memory. The carbon monoxide, carbon dioxide, hydrocarbons, nitrogen oxides, and water emission levels are then displayed on the monitor 22 along with a stop-frame video image of the vehicle 28 in relation to the date and time of the emissions measurement. This is then permanently stored on magnetic media by video recorder 24. Any type of storage unit 24 may be utilized with the invention including digital image storage and the like. Thus, the carbon monoxide, carbon dioxide, hydrocarbons, nitrogen oxides, and water emissions of the vehicle 28 are remotely sensed, and an identifying image of the vehicle, such as a stop-frame video, is overlaid by the date, time, the number of the vehicle in a series of vehicles (if desired), and the various emission levels, while also simultaneously permitting real-time reading of the data at the monitor 22. The computer system 17 may be designed to actually read the vehicle license plate using currently available optical character recognition software, or the operator of the system may read the information from the monitor 22 and then type this information and the license plate number into a computer data base. If the computer 17 or associated equipment is on-line with the Department of Motor Vehicles license registration data bank, the vehicle type, model, and year can also be displayed on the video image, along with the mandatory, if any, emission requirements of the state. In this manner, a particular vehicle could be identified as complying or not complying with state emission requirements immediately at the time and site of measurement, or at a later time if desired.

In more particular reference to FIG. 1, any available ultraviolet and infrared radiation source may be utilized with the present invention, along with a mechanism for directing the radiation beam 15 across the roadway 26. In the present invention, a preferred infrared radiation source 13 includes a commercial gas dryer ignitor, General Electric number WE4X444. A preferred ultraviolet radiation source includes a deuterium arc lamp or xenon arc lamp 12 emitting ultraviolet radiation therefrom. One manner of directing the ultraviolet and infrared radiation beams from the sources 12 and 13, respectively, includes the use of a reflective mirror 14 to direct the collimated beam of infrared radiation from the infrared source 13 across the roadway 26. A dichroic mirror or prism is provided in the form of a mirror 19 through which infrared radiation from the infrared source 13 passes so as to blend with the reflected ultraviolet beam to form a combined collimated beam 15. Another preferred embodiment of the present invention includes the use of a narrow angle CaF prism, with the sources 12 and 13 positioned at appropriate angular alignments to the prism so that a combined collimated beam 15 is emitted therefrom. With such a prism, the infrared radiation is hardly bent when passing therethrough, although the ultraviolet radiation is bent at a considerable angle. The appropriate arrangement of the sources 12, 13 relative to such a prism (not illustrated) would enable the ultraviolet beam to be exactly combined with the infrared beam in the collimated beam 15.

Figure 2:
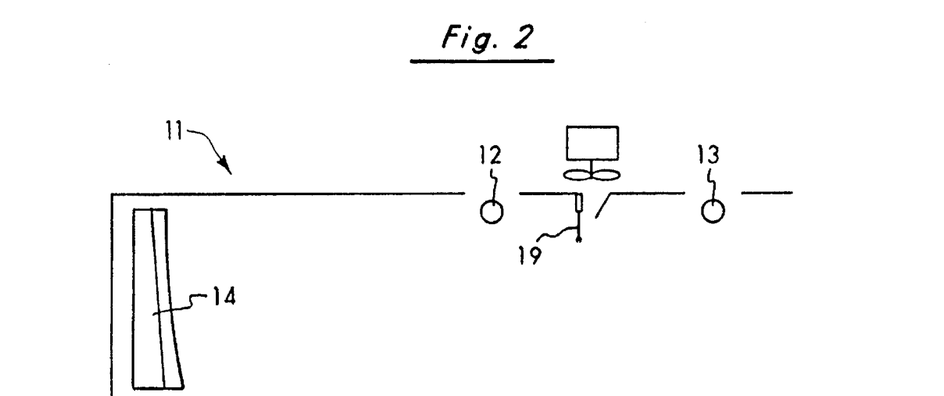
FIG. 2 is a schematic diagram of one preferred embodiment of a light source 11 for use in the remote measuring and monitoring system of the present invention.

A second, and more preferred, embodiment of the present invention is illustrated in FIG. 2, which illustrates the use of a dichroic mirror 19, which reflects ultraviolet radiation and passes infrared radiation.

Figures 3, 4, 5:
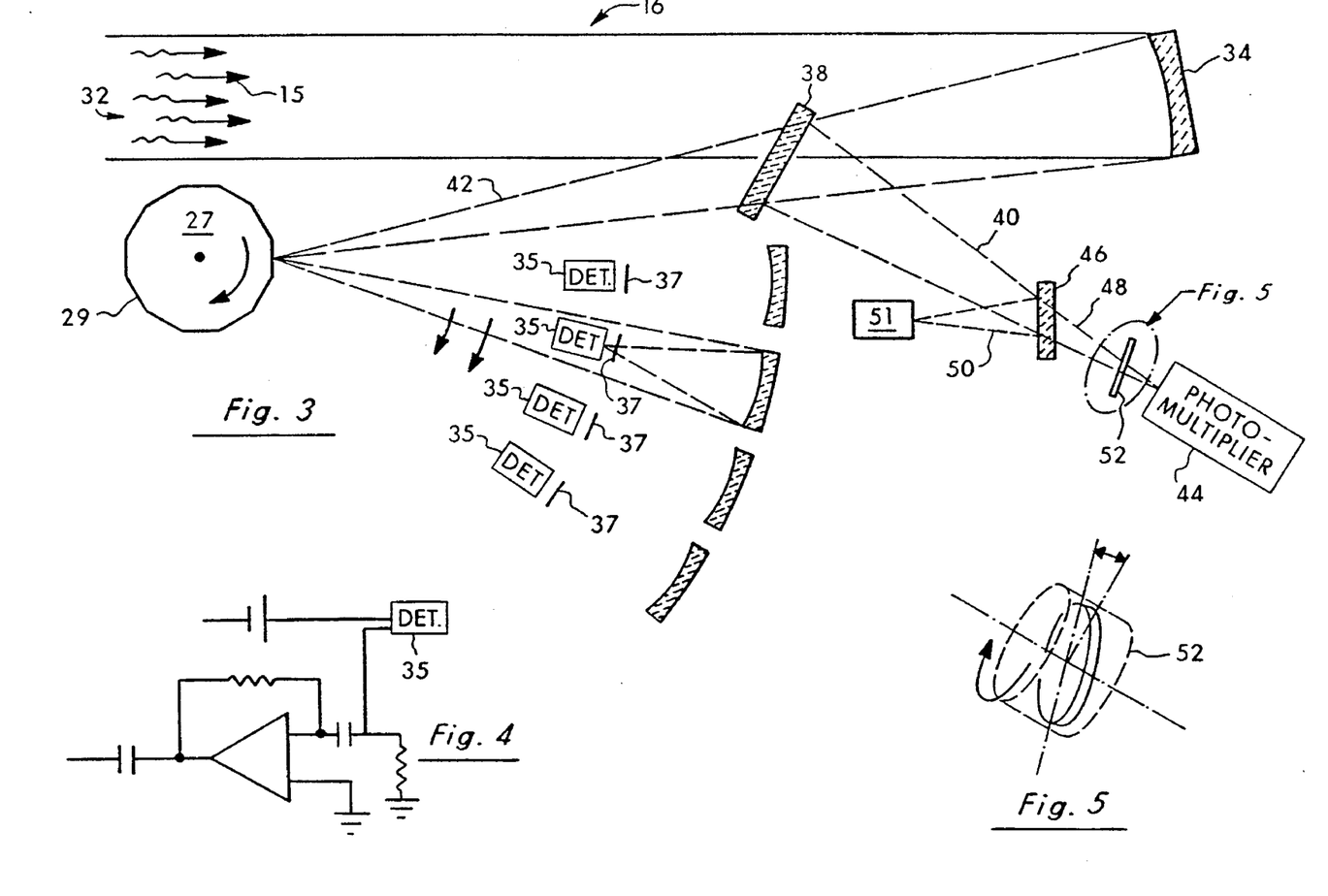
FIG. 3 is a schematic diagram of one preferred embodiment of a detector unit 16 for use in the remote measuring and monitoring system of the present invention.
FIG. 4 is a schematic diagram of a circuit for use in the infrared detectors of the present invention.
FIG. 5 is a schematic diagram of a tilting filter for use in the ultraviolet detection of $NO_x$.

With more particular reference to FIG. 3 and one preferred embodiment of the detector unit 16, an opening area 32 is provided for receiving the collimated beam 15. The opening area 32 is arranged such that as the collimated beam 15 enters therethrough, it is focused by an adjustable mirror 34 onto a beam splitter 38 (e.g., a beam splitter composed of CaF and appropriate overcoatings). While not shown, a CaF prism may also be utilized to divide the collimated beam 15 into two beams, one ultraviolet beam 40 and one infrared beam 42. As previously indicated, using a CaF narrow angle prism, infrared is hardly bent while the ultraviolet is bent at a considerable angle. Thus, the prism functions as a beam splitter to divide the ultraviolet and infrared portions from the collimated beam 15. The ultraviolet beam 40 is directed to an ultraviolet photomultiplier device 44 that functions to measure the absorption of ultraviolet in the roadway 26 exterior to the detector unit 16.

In the illustrated embodiment, an additional beam splitter 46 is provided to divide the ultraviolet beam 40 into two components, one component 48 being directed onto the photomultiplier 44 while another component 50 is directed onto a second photodetector 51 used for measuring background radiation. In one preferred form, a tilting interference filter 52 mounted at an angle on a rapidly rotating shaft is employed to generate a DC electrical signal in the absence of $NO_x$, but provides an AC electrical signal in the presence of $NO_x$. With AC coupled electronics, only $NO_x$ is observed by the photomultiplier device 44. The photomultiplier unit 44 is designed to provide a first electrical signal indicative of the absorption of ultraviolet radiation from the collimated beam 15 by the vehicle exhaust 30.

Now, with more particular reference to FIGS. 2 and 3, the detector unit 16, with an opening area 32 is provided to observe across a road 26 across which is transmitted infrared radiation and ultraviolet radiation in a single beam 15. Beam 15 is created using two separate light sources, infrared radiation from source 13 and ultraviolet radiation from source 12. The infrared and ultraviolet radiation are combined into the single beam 15 by a dichroic mirror 19. The dichroic mirror 19 is overcoated for ultraviolet radiation reflection, and passes infrared radiation, thereby passing infrared radiation and reflecting ultraviolet radiation. In the detector unit 16, the beam 15 is split into ultraviolet radiation 40 and infrared radiation 42 by a substantially identical dichroic mirror 38. The ultraviolet radiation 40 is then detected with an appropriate interference filter 52 and photomultiplier tube 44, as described above.

The infrared beam 42 continues through the detector unit 16 and is directed onto a rotating mirrored surface 27, for example, a rotating polygon structure such as a dodecagon having reflective mirrors 29 covering each of its sides. The rotating mirrored surface 27 reflects the beam 42 to each of the infrared photodetectors 35 in sequence. It should be noted that the rotating reflector 27 serves to time-multiplex the beam 42 to each of the photodetectors 35. In other words, given a system with N photodetectors, each photodetector receives essentially the full intensity of the infrared beam 42 during 1/Nth of any temporal period. Due to the performance characteristics of typical infrared photodetectors, it has been found that time-multiplexing results in greater sensitivity and accuracy than if each photodetector receives 1/Nth of the intensity of the infrared beam at all times.

A separate sensor assembly is provided for each chemical species in the exhaust to be monitored. Each sensor assembly consists of a photodetector 35 and a filter 37 selected to pass a wavelength indicative of the chemical species being monitored by the particular sensor assembly. For example, a filter 37 having a wavelength of 3.9 microns can be used for the reference channel, 4.3 microns for $CO_2$, 4.6 microns for CO, and 3.3–3.4 microns for hydrocarbons. For example, a liquid nitrogen-cooled indium antimonide photovoltaic detector or a lead selenide detector operated at or below ambient temperature can be used for each of the infrared detectors 35.

Referring back to the ultraviolet beam 40 and the photomultiplier unit 44, $NO_x$ in the predominantly emitted form of nitric oxide, NO, is measured by making use of the ultraviolet absorption in the wavelength range of about 230 nm. The use of ultraviolet absorption for NO has several advantages. These advantages include an ultraviolet absorption coefficient about 1000 times larger than an infrared absorption coefficient, giving rise to larger signals. Moreover, there is no interference from water vapor in the ultraviolet. The atmosphere is optically transparent, but ultraviolet radiation from the sun is irrelevant because the stratospheric ozone layer cuts out most of the ultraviolet radiation. Finally, solar-blind ultraviolet-detecting photomultiplier tubes as utilized in the unit 44 are available that are very sensitive and stable. This means that very low (i.e., eye safe) levels of ultraviolet radiation can be used for detection in the detector unit 16.

In operation, the detector unit 16 is set up preferably along a single-lane highway with the collimated ultraviolet and infrared beam 15 located approximately 10 inches above the roadway. The computer 17 monitors the infrared and ultraviolet signal intensities of the reference channel, and the signals are optimized by alignment of the source 11 and the detector unit 16. Upon entry of a vehicle 28 into the optical path of the beam 15, a drop in the voltage from the reference channel signals the presence of the vehicle 28. Voltages from each of the other signal channels (i.e., the NO detector 44, the detectors for CO, $CO_2$, HC, and $H_2O$, and the reference detector 35) that were acquired prior to the vehicle 28 interrupting the beam 15 are stored by the computer 17. As the vehicle 28 exits the beam 15 so that the beam 15 is again received by the detector unit 16, the computer 17 once again begins to acquire a stream of voltage samples from each of the sensors over time. The computer 17 continues to sample voltages from each of the sensors for a period of approximately 0.1 to about 1.0 second after the vehicle 28 exits the beam 15 in the preferred embodiment. The signals from the sensors are averaged by the computer over a temporal period of approximately 1 millisecond to 20 milliseconds for each sample, with about 10 milliseconds being preferred. By thus averaging the signal a better signal-to-noise ratio is obtained.

Figure 7:
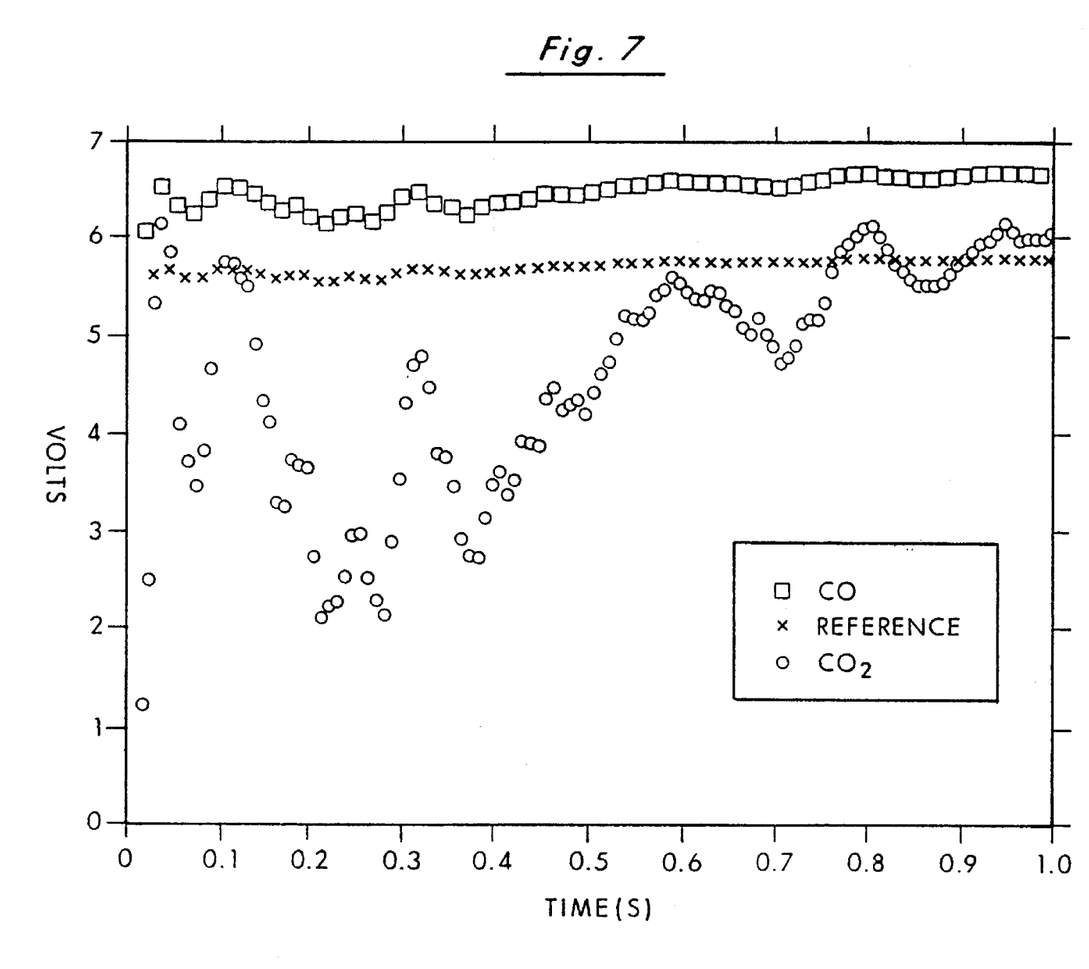
FIG. 7 is a graph showing sample voltage data as a function of time from the carbon monoxide sensor, the carbon dioxide sensor, and the reference sensor for a 1983 Oldsmobile traveling at 20 mph.
Figure 8:
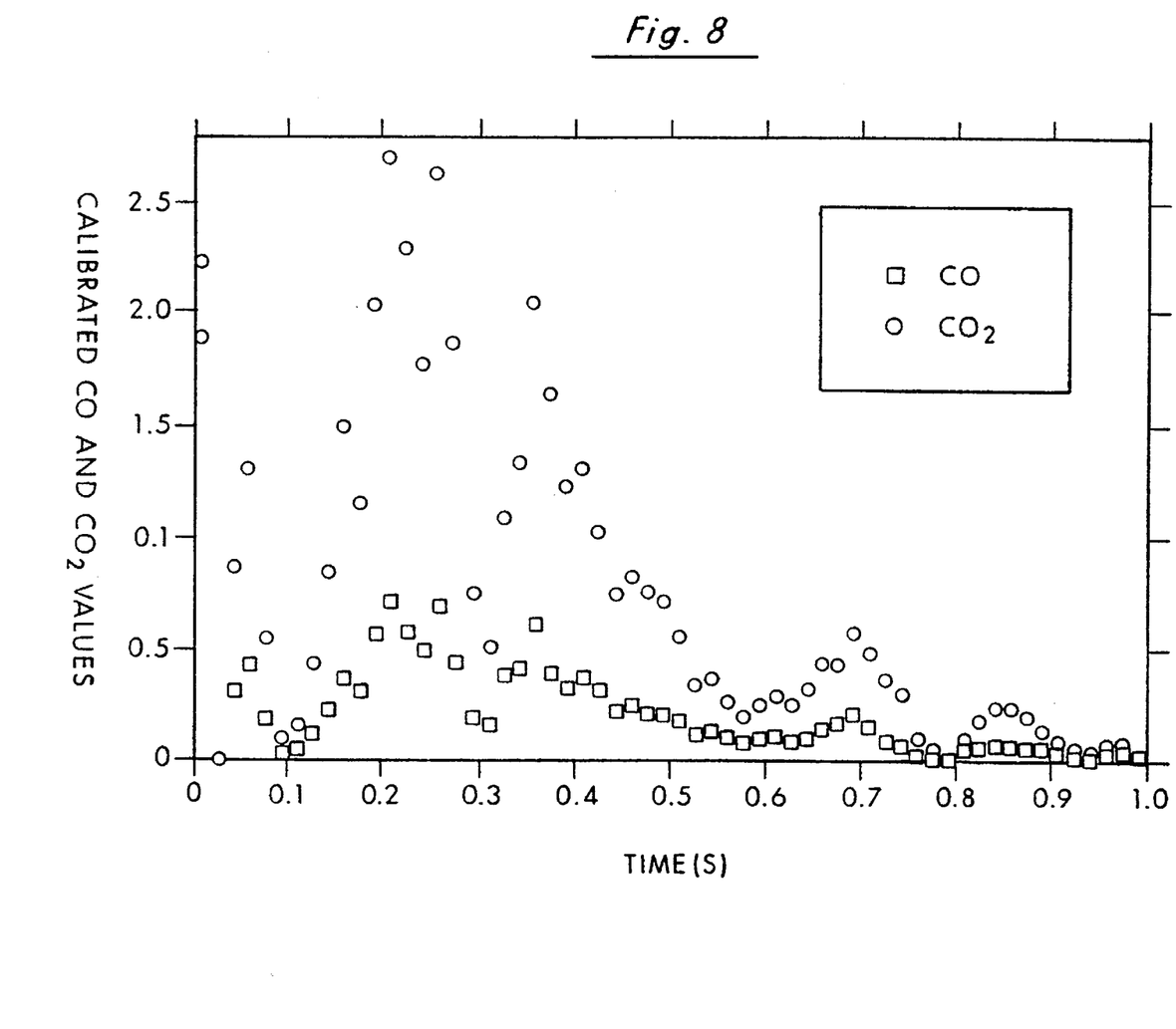
FIG. 8 is a graph showing the raw data from FIG. 7 converted to calibrated carbon monoxide and carbon dioxide values.
Figure 9:
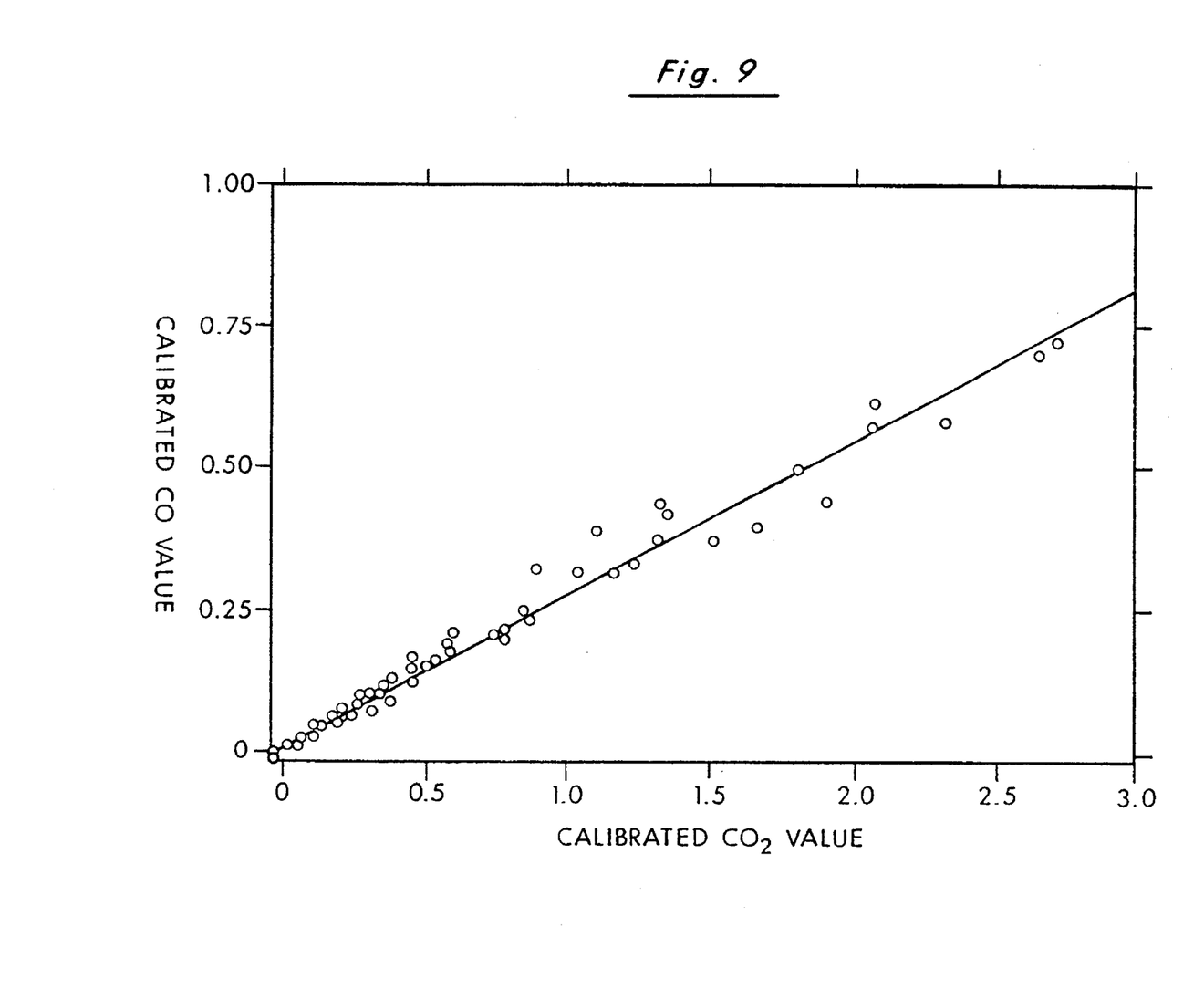
FIG. 9 is a correlation graph in which the calibrated CO and $CO_2$ values for each sample in FIG. 8 have been plotted. The slope of the line found by least-squares regression is the $CO/CO_2$ ratio, or Q.

The data analysis performed by the computer 17 can be better understood by beginning with a simplified system having only a carbon dioxide channel, a carbon monoxide channel, and a reference channel. FIG. 7 is a graph showing sample voltage data as a function of time from the carbon monoxide sensor, carbon dioxide sensor, and reference sensor for a 1983 Oldsmobile traveling at 20 mph. The raw data is then normalized by computing the ratios of the CO and $CO_2$ voltages to the reference voltages and rescaling these arbitrary units into calibrated CO and $CO_2$ values by the use of a calibration curve determined in a laboratory utilizing special flow cells with controlled mixtures of CO and $CO_2$. The calibration curve compensates for the performance characteristics of the filters and photodetectors, as well as for the relative degree of absorption at the wavelengths used in the system by carbon dioxide and carbon monoxide. FIG. 8 is a graph showing the raw data from FIG. 7 converted to calibrated carbon monoxide and carbon dioxide values. FIG. 9 is a correlation graph in which the calibrated CO and $CO_2$ values for each sample in FIG. 8 have been plotted. The computer 17 calculates the slope of this line by least-squares regression. The slope of this line, Q or $Q_{CO}$, is the $CO/CO_2$ ratio by moles.

An automobile can be considered as a device in which fuel containing carbon and hydrogen (formula $CH_n$) is burned with air whose approximate formula for this purpose is given as $0.21\ O_2 + 0.79\ N_2$ in a combustion chamber to derive power. The combustion products are sometimes further burned on a catalyst or in the exhaust system. However, if hydrocarbon and $NO_x$ emissions are considered to be small compared to the CO, $CO_2$, and nitrogen concentrations emanating from the tailpipe, the combustion process takes the form:

$$CH_n + m(0.21O_2 + 0.79N_2) \rightarrow \frac{n}{2}(H_2O) + aCO + bCO_2 + 0.79mN_2 \quad (1)$$

Carbon balance applied to equation (1) requires:

$$a+b=1 \quad (2)$$

Oxygen balance applied to equation (1) requires:

$$0.42m = \frac{n}{2} + a + 2b \quad (3)$$

The definition of Q, discussed above, provides:

$$Q = \frac{a}{b} \quad (4)$$

When a and b are determined in terms of Q, one obtains:

$$a = \frac{Q}{1+Q} \quad (5)$$

and $$b = \frac{1}{1+Q} \quad (6)$$

Thus, with a knowledge of n and Q, the molar coefficients in the balanced combustion equation are readily determined. These quantities are in turn used to obtain other derived quantities.

If $CH_2$ is used for the empirical formula of the fuel, then n in equation (1) is 2, and furthermore:

$$m = \frac{1 + a + 2b}{0.42} \quad (7)$$

One then obtains:

$$\text{dry } CO_2 \text{ fraction} = \frac{b}{1 + 0.79m} \quad (8)$$

Note that any percentage errors in m caused by the assumption of n=2 will be halved for most vehicles since n is divided by 2 in this derivation. Upon substitution for b and m, one obtains:

$$CO_2 \text{ fraction} = (1/(1+Q))/(1+0.79(3+2Q)/0.42(1+Q)) \quad (9)$$

After multiplying throughout by 0.42(1+Q):

$$\% CO_2 = \frac{42}{0.42 + 0.42Q + 2.37 + 1.58Q} = \frac{42}{2.79 + 2Q} \quad (10)$$

Similarly, $$\% CO = \% CO_2 Q = \frac{42Q}{2.79 + 2Q} \quad (11)$$

Thus, the percentages of carbon monoxide and carbon dioxide in the exhaust can be determined from the slope of the line, Q, as shown in FIG. 9.

This type of analysis can be extended to additional channels, such as for hydrocarbons or nitrogen oxides. For example, assume that a sensor for hydrocarbons is added. A series of raw data samples is acquired by the computer 17 from the hydrocarbons sensor for a predetermined period after the vehicle passes through the beam 15, similar to that shown in FIG. 7. The raw data is normalized by the reference channel and calibrated, in the manner previously discussed, to produce calibrated HC values similar to FIG. 8. The computer then performs a least-squares regression of the calibrated HC values against the calibrated $CO_2$ values, similar to FIG. 9. The slope of the line, $Q_{HC}$, is the path-independent ratio of $HC/CO_2$ by moles. Data from the carbon monoxide channel and the carbon dioxide channel are processed by the computer as previously discussed to determine the $CO/CO_2$ ratio, or $Q_{CO}$, as before. The percentages of CO, $CO_2$, and hydrocarbons can be calculated from $Q_{co}$ and $Q_{HC}$ as follows:

$$\% CO_2 = \frac{42}{2.79 + 2Q_{CO} - 0.37Q_{HC}} \quad (12)$$

$$\% CO = \% CO_2 Q_{CO} \quad (13)$$

-continued $$\% \text{ HC} = \% \text{ CO}_2 Q_{HC} \quad (14)$$

Similarly, if a $NO_x$ channel is added to the apparatus, the $NO_x/CO_2$ ratio or $Q_{NOx}$ is calculated in the same manner by least-squares regression from the calibrated $NO_x$ and $CO_2$ sample data. The percentage of $NO_x$ in the exhaust is determined as follows:

$$\% \text{ NO}_2 = \frac{42 Q_{NOx}}{2.79 + 2Q_{CO} - 0.37 Q_{HC}} \quad (15)$$

$NO_x$ is normally such a small percentage of the exhaust gases in comparison to $CO_2$, CO, and hydrocarbons that equations (12), (13), and (14) continue to be good approximations for these gases. It should be noted that additional sensor channels can be readily included in the present system to provide similar analyses for other chemical constituents of the vehicle exhaust.

The system can be adapted to provide an indication of the exhaust system temperature using an infrared sensor with a 2.8 to 2.9 micron filter to measure the amount of water present in the exhaust. Cold engines tend to generate substantially more pollutants than warm engines, and also to produce water droplets rather than vapor as would an engine operating above 100° C. A one to one molar ratio of water vapor to CO and $CO_2$ would indicate a warm engine, while a smaller ratio would indicate a cold engine. By measuring the amount of water vapor as compared to CO and $CO_2$, it can be determined whether an engine was running with high emissions because it was cold or because the vehicle emission systems were malfunctioning.

In addition, this water sensor can be used to measure the amount of liquid-phase water in the form of droplets or steam present in the exhaust to flag possibly erroneous readings from the hydrocarbons channel. Water droplets also show strong absorption at 3.3 and 3.4 microns, which is the wavelength used by the hydrocarbons channel. Thus, water droplets from a cold engine can be erroneously interpreted by the hydrocarbons sensor as a very large hydrocarbons emission. The water channel has the advantage of accurately measuring water without hydrocarbons interference. A reading from the water sensor showing large amounts of water droplets can be used as a flag to indicate that the corresponding reading from the hydrocarbons sensor is probably inaccurate and should be ignored.

Solid particulate matter is becoming more and more a matter of concern. It is abundantly clear that the system of the present invention may also be easily adapted to measure the opacity of the exhaust of a vehicle, and thereby provide an indication of the nongaseous particulate matter being generated by the vehicle engine.

Figure 6:
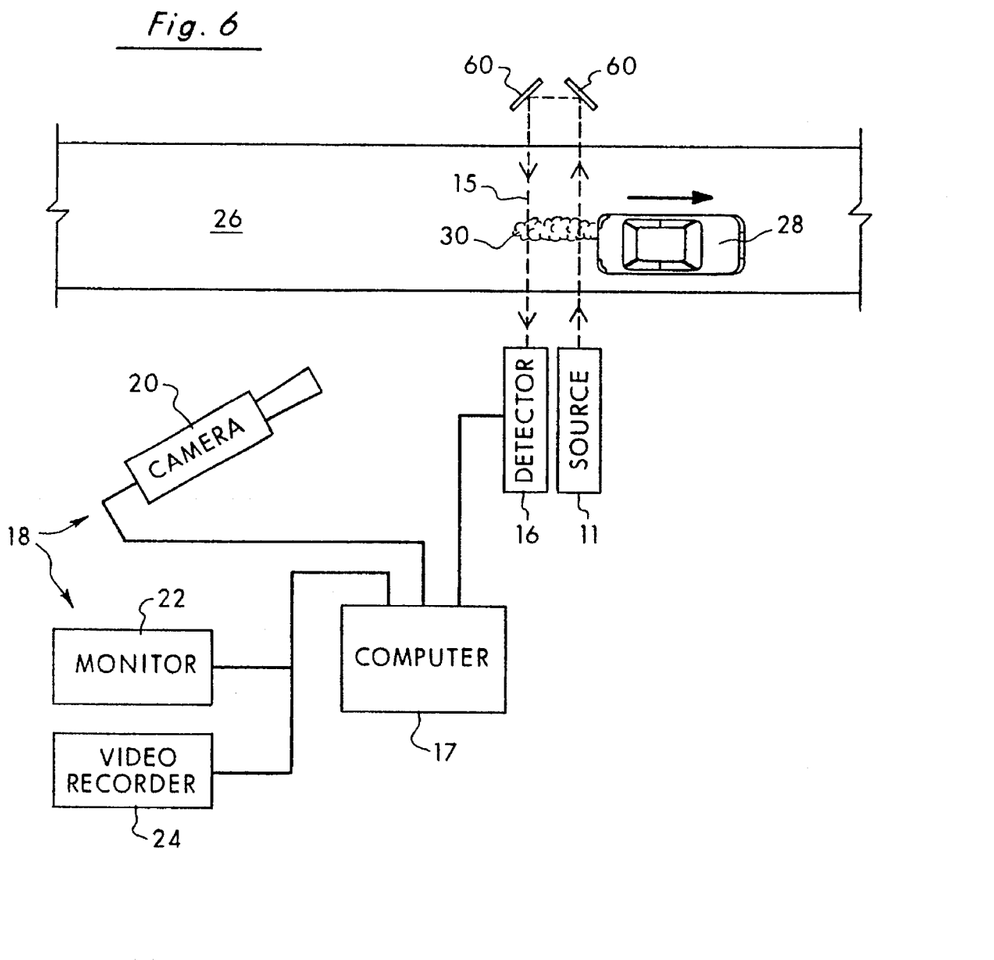
FIG. 6 is a schematic diagram of an alternative embodiment of the system in which the source and detector are located on the same side of the roadway. A reflector 60 located on the opposite side of the roadway is used to reflect the beam from the source 11 to the detector unit 16 with two passes through the vehicle exhaust.

Currently contemplated state of the art modifications include the incorporation of both the infrared and ultraviolet radiation sources and the detector system in a single unit or in side by side units on the same side of the roadway 26 as shown in FIG. 6. In such an instance the source 11 sends the beam 15 out to one or more reflectors 60 that return the beam 15 to the detector unit 16 for processing as detailed above. This arrangement simplifies operation of the system (after initial setup) by having both the detector 16 and source 11 adjacent to one another on one side of the roadway. In addition, this arrangement increases the absorption signal by providing two passes of the beam 15 through the vehicle exhaust plume 30 on-road.

Figure 10:
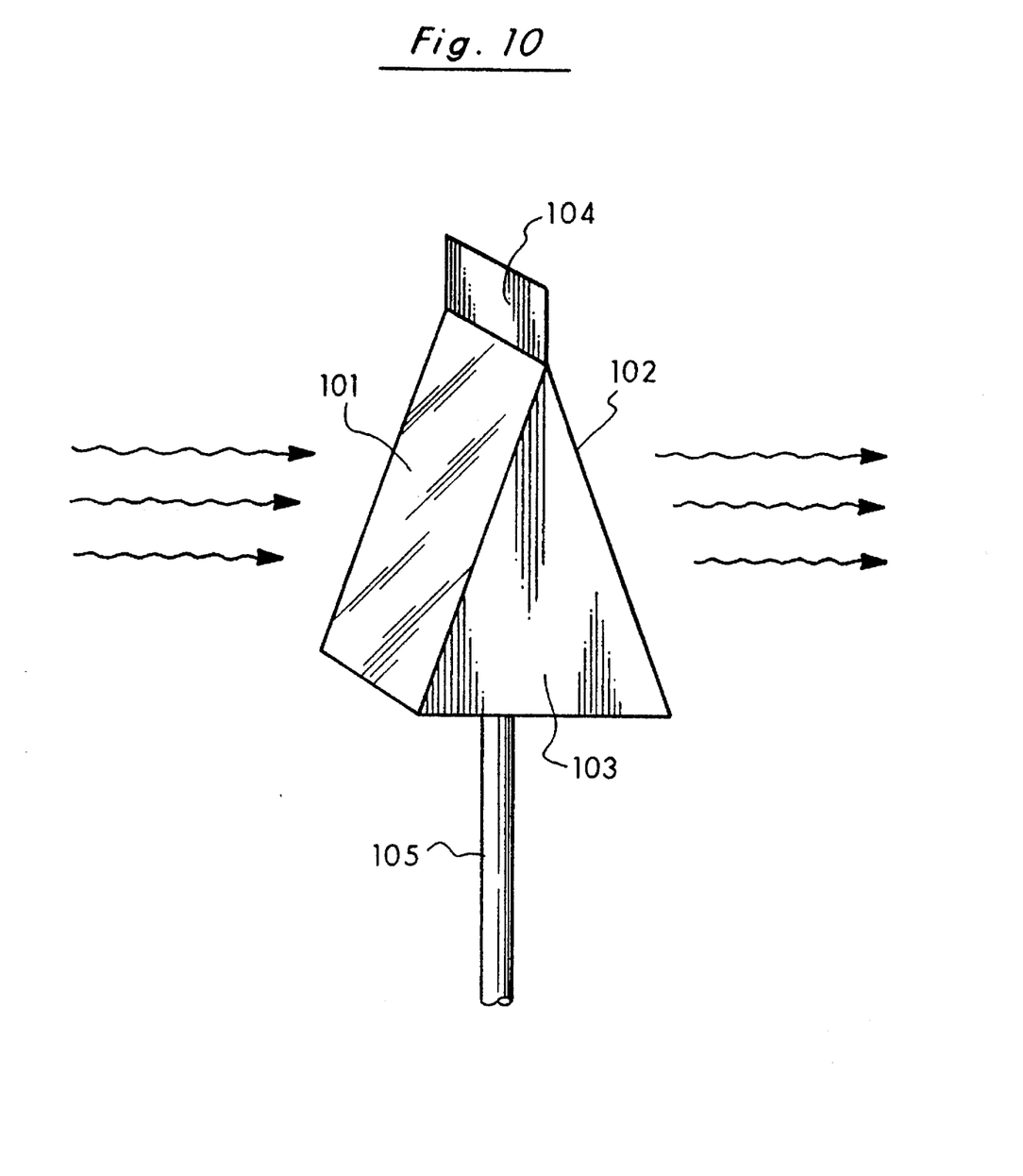
FIG. 10 is a perspective view of the wedge-shaped gas cell used to calibrate the system.

FIG. 10 shows the wedge-shaped gas cell used for calibration of the system. The cell has two transparent windows 101 and 102 that permit a beam of light to pass through a wedge-shaped cavity within the cell. The remaining walls 103 of the cell are typically made of an opaque material, such as aluminum. The cavity within the cell between the transparent windows 101 and 102 is filled with a known mixture of all of the gases monitored any given configuration by the system. For example, a typical gas mixture is 47% CO, 47% $CO_2$, and 6% propane for a system having CO, $CO_2$, and hydrocarbons channels. A handle 105 attached to the bottom of the cell is used to gradually slide the cell across the path of the beam 15 in the detector unit 16. The triangular or wedge-shaped cross-section of the cell provides variation in length of the optical path for the beam 15 through the cell as the cell is moved across the beam 15. An opaque blade 104 extends forward along the leading edge of the cell. The blade 104 is the first portion of the calibration cell to enter the beam 15 and provides the same zero reference to begin the calibration process as is provided by a passing automobile. As the cell is inserted further into the beam 15, absorption of the beam by the gases within the cell progressively increases as the optical path through the cell correspondingly lengthens. The computer 17 continually samples the output of the sensors for each channel as the calibration cell is inserted. Since the ratio of the gas mixture within the cell remains constant, the samples from the CO and $CO_2$ channels during calibration should trace out a relatively straight line when plotted in the form of a correlation graph such as FIG. 9. In particular, the sample points should begin near the lower left corner of the graph when the optical path through the cell is at a minimum, and then proceed upward and to the right along a line as the length of the optical path increases. The slope of this line, $Q_{CO}$, is then compared against the known ratio of concentrations CO and $CO_2$ within the cell for the purpose of determining an appropriate calibration factor for carbon monoxide. A similar analysis is performed for the ratio of hydrocarbons to $CO_2$ if the unit has a hydrocarbons channel, and for the ratio of NO to $CO_2$ if the unit has a NO channel.

In one possible alternative embodiment, the calibration cell has a series of steps along its length to provide regions of differing cross-sectional widths. For example, a stepped triangular cross-section can be used.

Figure 11:
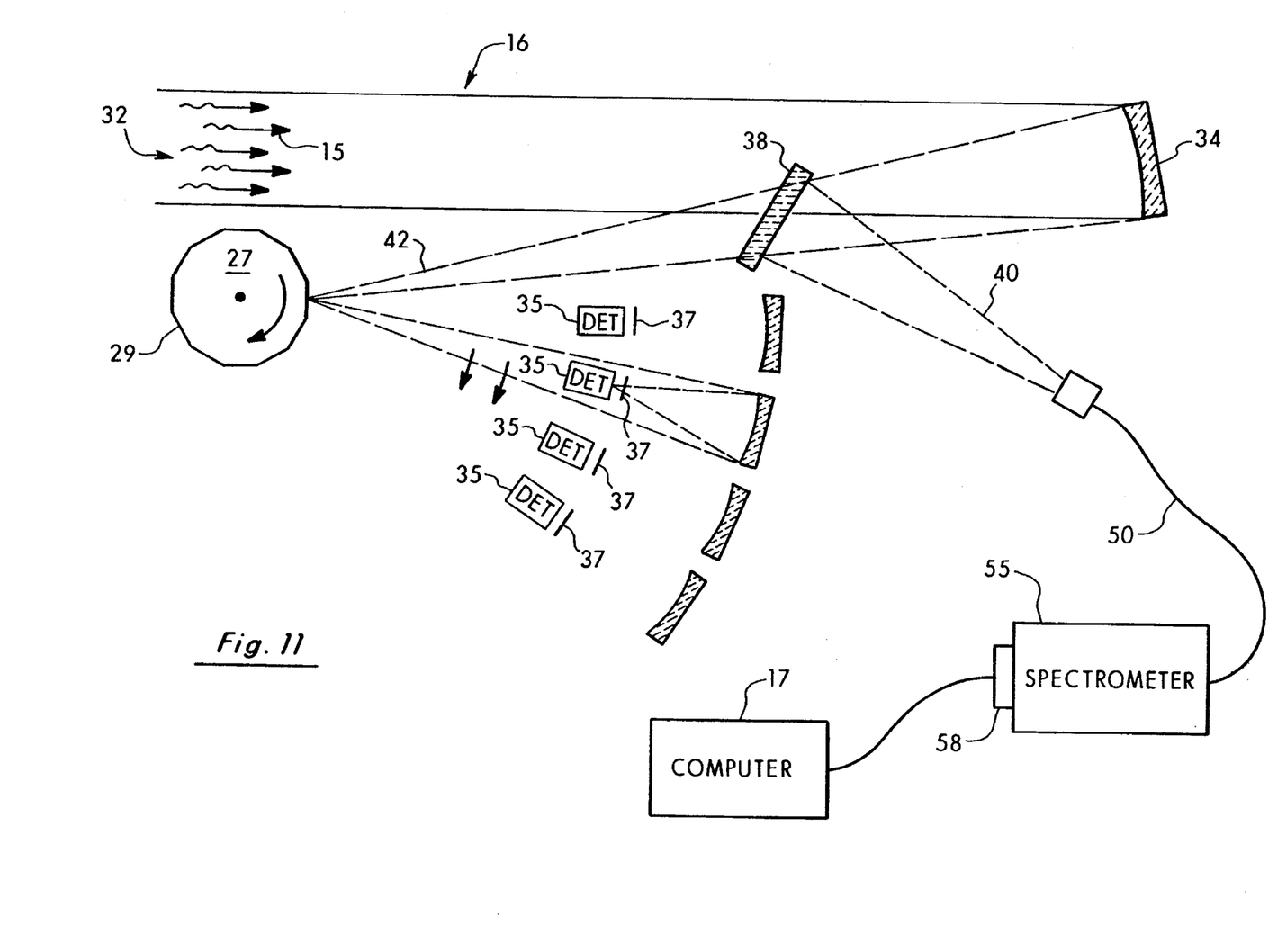
FIG. 11 is a schematic diagram of an alternative embodiment of the detector unit 16 using an ultraviolet beam and a spectrometer to measure the concentration of nitric oxide (NO) in the vehicle exhaust.

FIG. 11 is a schematic block diagram of an alternative embodiment of the detector 16 in which the filter 52 and photomultiplier tube 44 have been replaced with a spectrometer 55 to measure the concentration of nitric oxide (NO). The remainder of the system is largely unchanged. As before, the light source 11 transmitts a collimated beam 15 combining both infrared and ultraviolet light through the exhaust plume 30 behind the vehicle 28. The detector 16 includes a beamsplitter 38 to separate the infrared beam 42 from the ultraviolet beam 40. The ultraviolet beam 40 is then diffracted by means of a prism or diffraction grating within the spectrometer 55. The resulting spectrum is directed onto an array of photodiodes 58, so that each photodiode generates a voltage proportional to the intensity of the light within a corresponding narrow segment of the spectrum.

Figure 12:
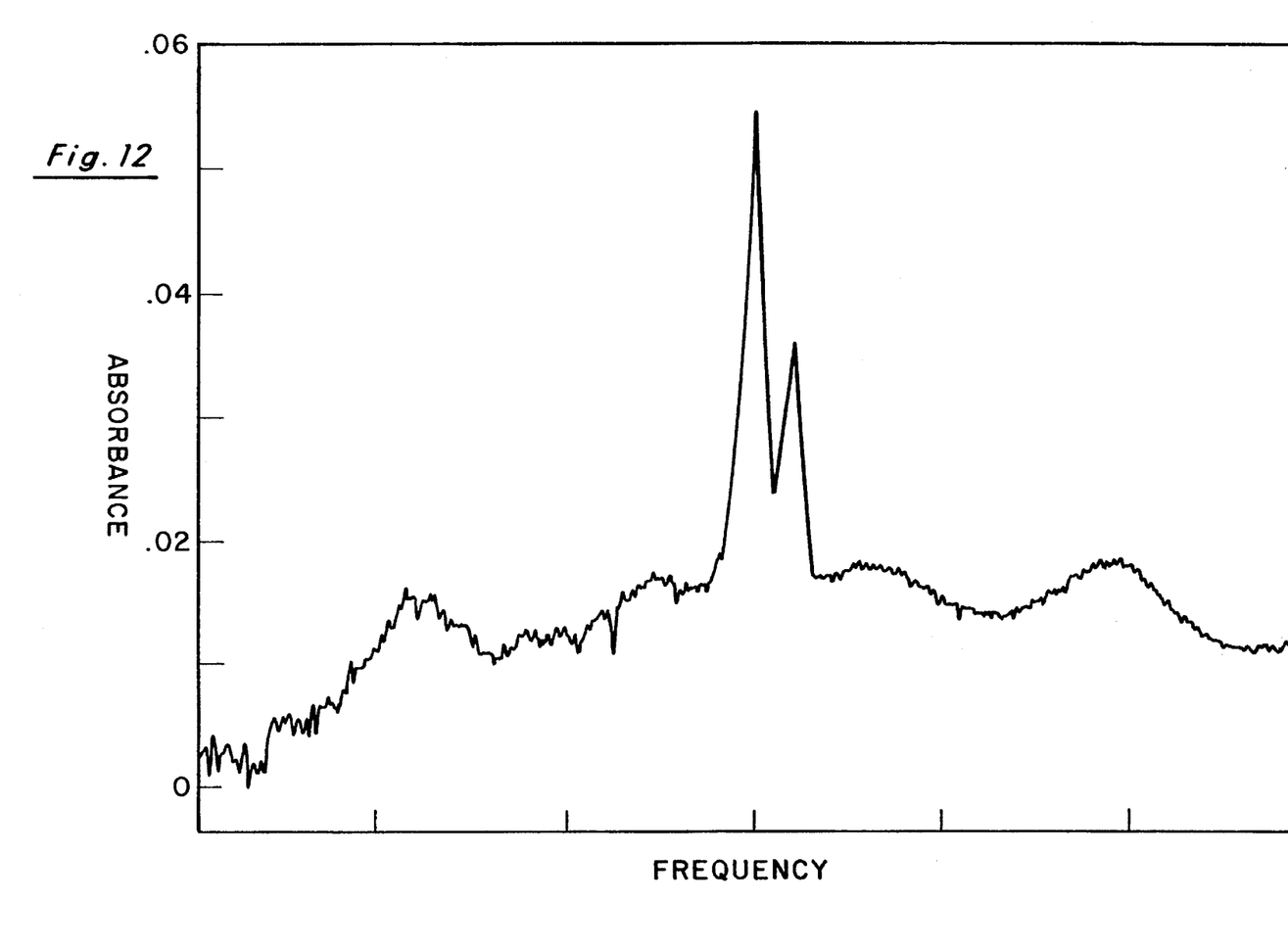
FIG. 12 is a chart showing absorbance of the ultraviolet beam as a function of frequency measured by the spectrometer.

FIG. 12 is a graph of a typical absorbance spectrum produced by the spectrometer 55 from the ultraviolet beam passing through the exhaust plume of a moving vehicle. This graph clearly shows an absorbance peak at a wavelength of approximately 227 nm. Therefore, the output signals from the corresponding elements in the photodiode array 58 can be employed as an indication of the concentration of NO in the exhaust plume. The output signals from other photodiodes in the array outside of the peak can be used to establish a reference signal indicating total absorption of the ultraviolet beam by the exhaust. The output signals from the photodiode array 58 are converted into digital form and periodically sampled by the computer 17. Alternatively, the photodiode array 58 could be replaced with a rapid slit scanner and a photomultiplier tube. As previously described, the computer 17 typically samples the output signal from each of the infrared sensors and the spectrometer for a predetermined period following resumption of the beam reception by the detector after a moving vehicle interrupts the beam.

The $NO/CO_2$ ratio or $Q_{NO}$ is calculated by least-squares regression from calibrated NO and $CO_2$ sample data. The percentage of NO in the exhaust is determined as follows, similar to equation (15):

$$\% NO = \frac{42 Q_{NO}}{2.79 + 2Q_{CO} - 0.37 Q_{HC}} \qquad (16)$$

NO is normally such a small percentage of the exhaust gases in comparison to $CO_2$, CO, and hydrocarbons that equations (12), (13), and (14) continue to be good approximations for these gases.

As previously stated, equations (1) through (16) am based on assumptions that hydrocarbon and $NO_x$ (or NO) emissions are very small compared to the CO, $CO_2$, and nitrogen concentrations emanating from the vehicle tailpipe. Alternative derivations of these equations can be used. For example, the following combustion reaction includes NO and unburned hydrocarbon emissions in the vehicle exhaust:

$$CH_n + m(0.21 O_2 + 0.79 N_2) \rightarrow \qquad (17)$$

$$\frac{n}{2} H_2O + aCO + bCO_2 + cCH_2 + dNO + \left(0.79m - \frac{d}{2}\right) N_2$$

Unburned hydrocarbons are assumed to be emitted as a mixture of hydrocarbons having an average empirical hydrogen-to-carbon ratio of 2:1, which can be approximated as $CH_2$. Again, n=2 for fuel having an empirical formula of $CH_2$. A carbon balance applied to equation (17) requires:

$$a+b+c=1 \qquad (18)$$

An oxygen balance applied to equation (17) requires:

$$0.42\, m = a + 2b + 1 + d \qquad (19)$$

The following Q ratios can then be derived:

$$Q = Q_{CO} = \frac{a}{b} = \frac{CO}{CO_2} \qquad (20)$$

$$Q_{HC} = \frac{c}{b} = \frac{HC}{CO_2} \qquad (21)$$

$$Q_{NO} = \frac{d}{b} = \frac{NO}{CO_2} \qquad (22)$$

One then obtains the following dry percentage calculations:

$$\% CO_2 = \frac{42}{2.79 + 2Q + 0.42 Q_{HC} + Q_{NO}} \qquad (23)$$

and $$\% NO = \frac{42 Q_{NO}}{2.79 + 2Q + 0.42 Q_{HC} + Q_{NO}} \qquad (24)$$

Equations (17) through (24) will typically produce results that are essentially the same as equations (1) through (16) for most vehicles.

A quartz optical fiber 50 can be employed to transport the ultraviolet beam 40 from the beamsplitter 38 to the port of the spectrometer 55, as shown in FIG. 11. This simplifies packaging of the spectrometer within a common housing with the remainder of the detector components, and also provides greater flexibility in adjusting optical alignment.

The spectrometer has both advantages and disadvantages. The primary disadvantages are substantially increased cost and complexity of the system. The primary advantage is the ability of the spectrometer to achieve higher resolution than the filter/photomultiplier arrangement described above. The first embodiment shown in FIG. 3 works well in distinguishing vehicles that emit gross amounts of pollution (>3,000 ppm NO) from relatively clean cars (approximately 1,000 ppm NO). However, the second embodiment significantly increases the signal-to-noise ratio for NO detection by about an order of magnitude. Another advantage is that the spectral data produced by the spectrometer can be used to unequivocally identify a specific compound (e.g., nitric oxide) based on a unique combination of known peaks associated with the compound. This helps to identify interferences between compounds and can also be used to identify unknown compounds that may be present in vehicle exhaust, based on the shape and location of absorption peaks in the UV spectrum. The system can also be readily adapted to detect compounds other than NO having absorption peaks in the UV region, such as benzene, toluene, xylene, and $NO_2$.

As can be seen from the above, the present invention provides a unique system for the remote measuring and monitoring of emissions from moving motor vehicles. In particular, the present invention provides for a device that will simultaneously measure CO, $CO_2$, HC, NO, and $H_2O$ depending on a desired measurement. This particular invention allows a remote sensing and measuring system so that vehicles do not have to be stopped and can be spot-checked at any given time. Moreover, this particular system permits the visual display as well as permanent recording of such display of the actual vehicle, including license plate identification, which is displayed in conjunction with the exhaust measurements. Such a system could be utilized to enforce emission standards under real-use conditions and/or to simply obtain real-time measurements so as to permit vehicle owners to be made aware of necessary corrections of vehicle emissions. The capability of measuring nitrogen oxides and hydrocarbons levels is particularly useful, since there is presently no existing system available that allows such measurements, and such measurements are crucial to the whole emission picture of any given vehicle. The unique capability of measuring NO and hydrocarbons in conjunction with CO and $CO_2$, as well as identifying by license place number the specific vehicle responsible for such emissions for both immediate and future use is exceptionally beneficial, both from an emissions enforcement aspect as well as from environmental aspects to permit the actual owner and operator of the vehicle to be aware of real-time use emissions of the vehicle.

It is therefore seen that the present invention provides an improved remote gas analysis device for the detecting, measuring, and recording of emission levels of substantially all gaseous components in the exhaust, such as NO, CO, $CO_2$, HC, and $H_2O$ vapor, of in-use vehicles. It also simultaneously measures the temperature of the vehicle exhaust while also measuring the amount of specific gaseous pollutants. The system, as described, also includes in one embodiment, a visual recording device for recording the vehicle and test results.

While the invention has been particularly shown, described, and illustrated in detail with reference to preferred embodiments and modifications thereof, it should be understood by those skilled in the art that the foregoing and other modifications are exemplary only, and that equivalent changes in form and detail can be made therein without departing from the true spirit and scope of the invention as claimed, except as precluded by the prior art.

We claim:

1. A gas analysis system for detecting and measuring concentrations of gases in the exhaust of a moving motor vehicle comprising:

a source for producing and transmitting a beam of infrared radiation through at least a portion of said exhaust;

a detector having a plurality of infrared sensors for receiving at least a portion of said beam, each infrared sensor generating a signal indicative of the absorption of said infrared beam by said exhaust in a corresponding wavelength band; said infrared sensors including at least a first sensor for carbon monoxide, a second sensor for carbon dioxide, and a third sensor for hydrocarbons; and means responsive to said signals from said infrared sensors for:
(a) computing the ratio of carbon monoxide to carbon dioxide ($Q_{CO}$) and the ratio of hydrocarbons to carbon dioxide ($Q_{HC}$) from said infrared sensor signals; and
(b) computing the concentrations of said carbon monoxide, carbon dioxide, and hydrocarbons in the path of said beam through said exhaust from $Q_{CO}$ and $Q_{HC}$ based on the chemical composition of fuel for said motor vehicle.

2. The system of claim 1, wherein said detector further comprises means for time-multiplexing said infrared beam to each of said infrared sensors.

3. The system of claim 2, wherein said time-multiplexing means comprises a rotating reflector directing said infrared beam to each of said sensors in sequence.

4. The system of claim 2, wherein said time-multiplexing means comprises a rotating polygonal structure having reflective surfaces along the edges of said polygon to direct said infrared beam to each of said sensors in sequence.

5. The system of claim 1, wherein at least one of said infrared sensors comprises a photodetector with a filter passing a wavelength indicative of the gas to be detected by said sensor.

6. The system of claim 1, further comprising visual recording means aligned to record the end portion of said vehicle, including any vehicle identification material displayed on said vehicle.

7. The system of claim 1, wherein said computing means samples said signals from said infrared sensors for a predetermined period following resumption of beam reception by said detector after a moving vehicle interrupts said beam.

8. The system of claim 1, wherein said source and said detector are located on one side of a roadway, and said system further comprises at least one reflector located on the opposite side of said roadway to reflect said infrared and ultraviolet beam from said source to said detector.

9. The system of claim 1, further comprising an infrared sensor generating a signal indicative of the absorption of said infrared beam by water in said exhaust.

10. The system of claim 1, further comprising an infrared sensor generating a signal indicative of the total absorption of said infrared beam in said exhaust.

11. The system of claim 1, further comprising a calibration cell containing a known mixture of at least two of said exhaust gases, said calibration cell being removably insertable across the path of said beam between said source and said infrared sensors with the optical depth of said beam path through said gases in said calibration cell varying as said calibration cell is inserted across said beam path.

12. A gas analysis system for detecting and measuring concentrations of gases in the exhaust of a moving motor vehicle comprising:

a source for producing and transmitting a beam of infrared radiation through at least a portion of said exhaust;

a detector having a plurality of infrared sensors for receiving at least a portion of said beam, each infrared sensor generating a signal indicative of the absorption of said infrared beam by said exhaust in a corresponding wavelength band; said infrared sensors including at least a first sensor for carbon monoxide, a second sensor for carbon dioxide, a third sensor for hydrocarbons, and a reference sensor indicative of total absorption of said infrared beam by said exhaust; and means responsive to said signals from said infrared sensors for:
(a) computing the ratio of carbon monoxide to carbon dioxide ($Q_{CO}$) and the ratio of hydrocarbons to carbon dioxide ($Q_{HC}$) from said infrared sensor signals for a predetermined period following resumption of beam reception by said detector after said moving vehicle interrupts said beam; and
(b) computing the concentrations of said carbon monoxide, carbon dioxide, and hydrocarbons in the path of said beam through said exhaust from $Q_{CO}$ and $Q_{HC}$ based on the chemical composition of fuel for said motor vehicle.

13. The system of claim 12, wherein said detector further comprises a rotating reflector directing said infrared beam to each of said infrared sensors in sequence.

14. The system of claim 12, wherein at least one of said infrared sensors comprises a photodetector with a filter passing a wavelength indicative of the gas to be detected by said sensor.

15. The system of claim 12, wherein said source and said detector are located on one side of a roadway, and said system further comprises at least one reflector located on the opposite side of said roadway to reflect said infrared beam from said source to said detector.

16. The system of claim 12, further comprising visual recording means aligned to record the end portion of said vehicle, including any vehicle identification material displayed on said vehicle.

17. The system of claim 12, further comprising an infrared sensor generating a signal indicative of the absorption of said infrared beam by water in said exhaust.

18. The system of claim 12, further comprising a calibration cell containing a known mixture of at least two of said exhaust gases, said calibration cell being removably insertable across the path of said beam between said source and said infrared sensors with the optical depth of said beam through said gases in said calibration cell varying as said calibration cell is inserted across said beam path.

* * * * *